(12) United States Patent
Goto

(10) Patent No.: US 8,055,038 B2
(45) Date of Patent: Nov. 8, 2011

(54) IMAGE PROCESSING APPARATUS, IMAGE PROCESSING METHOD, AND MAGNETIC RESONANCE IMAGING APPARATUS

(75) Inventor: Takao Goto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 960 days.

(21) Appl. No.: 12/018,363

(22) Filed: Jan. 23, 2008

(65) Prior Publication Data
US 2008/0212863 A1 Sep. 4, 2008

(30) Foreign Application Priority Data

Jan. 26, 2007 (JP) ................................. 2007-016464

(51) Int. Cl.
*A61B 5/055* (2006.01)
(52) U.S. Cl. ........................................ 382/128; 382/131
(58) Field of Classification Search .................. 382/100, 382/128, 131, 308, 325
See application file for complete search history.

(56) References Cited

U.S. PATENT DOCUMENTS

| 6,175,655 | B1 * | 1/2001 | George et al. ................. 382/257 |
| 7,072,499 | B2 | 7/2006 | Deschamps et al. |
| 7,079,674 | B2 | 7/2006 | Paragios et al. |
| 7,229,412 | B2 | 6/2007 | Jacob et al. |
| 2007/0036434 | A1 * | 2/2007 | Saveliev ....................... 382/173 |
| 2008/0247622 | A1 * | 10/2008 | Aylward et al. ............... 382/131 |
| 2008/0279779 | A1 * | 11/2008 | Pruvot et al. .................... 424/9.4 |
| 2009/0226060 | A1 * | 9/2009 | Gering et al. ................. 382/128 |

OTHER PUBLICATIONS

Gerig et al, Nonlinear Anisotropic Filtering of MRI Data, IEE Transactions on Medical Imaging, Jun. 1992, pp. 221-232, 11(2).
Sethian, J.A., Level set method and fast marching methods, Cambridge University Press, 1999, pp. 87-101.
Saraswathy et al., ISMRM, 2006, p. 1609.
Toriwaki et al, Image Information Process, Corona Publishing Co., Ltd 2005, pp. 73-76 (along with English translation).

* cited by examiner

*Primary Examiner* — Stephen Koziol
(74) *Attorney, Agent, or Firm* — Armstrong Teasdale LLP

(57) ABSTRACT

An image processing method of performing an imaging process on an original image having a connection figure including a first figure and a second figure connected to the first figure to generate an extraction image of the first figure extracted, includes the steps of: obtaining a first image in which the connection figure in the original image is selectively extracted by performing a segmentation process on the original image; obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image; obtaining a third image by performing a segmentation process so as to selectively extract the third figure in the second image; obtaining a fourth image by performing a process of obtaining the difference between the first image and the third image; obtaining a fifth image by determining whether the size of a figure included in the fourth image obtained in the fourth image processing step is equal to or larger than a reference value, and when the size is equal to or larger than the reference value, eliminating the figure from the fourth image and, when the size is less than the reference value, processing the fourth image so as to leave the figure in the fourth image; and obtaining the extraction image by adding the third image and the fifth image.

20 Claims, 8 Drawing Sheets

(a)      (b)      (c)

IMAGE PROCESSING APPARATUS, IMAGE PROCESSING METHOD, AND MAGNETIC RESONANCE IMAGING APPARATUS

CROSS REFERENCE TO RELATED APPLICATIONS

This application claims the benefit of Japanese Patent Application No. 2007-16464 filed Jan. 26, 2007.

BACKGROUND OF THE INVENTION

The field of the present invention relates to an image processing apparatus, an image processing method, a magnetic resonance imaging apparatus, and a program for use in image processing. More particularly, the present invention relates to an image processing apparatus, an image processing method, a magnetic resonance imaging apparatus, and a program for performing an imaging process on an original image obtained so as to include a connection figure having a plurality of figures connected to each other, thereby generating an extraction image of a figure to be extracted in the plurality of figures.

An imaging apparatus such as a magnetic resonance imaging (MRI) apparatus is an apparatus for obtaining an image of a subject and displaying the image on a screen and is often used for medical purposes.

In the magnetic resonance imaging apparatus, an imaging region in a subject is placed in an imaging space in which static magnetic fields are generated, and spins of protons in the imaging region are aligned in the direction of the static magnetic fields, thereby generating a magnetization vector. By applying an RF pulse of resonance frequency, the nuclear magnetic resonance phenomenon is caused to flip the spins and change the magnetization vector of the protons. After that, a magnetic resonance (MR) signal generated when the flipped proton returns to the original state of the magnetization vector is received. On the basis of the received magnetic resonance signal, an image such as a slice image of the imaging region is reconstructed.

In the magnetic resonance imaging apparatus, to obtain information of the extending direction of a fiber such as a nerve fiber bundle in a subject, the head of the subject is scanned by the DTI (Diffusion Tensor Imaging), and DTI data set is generated. For example, the DTI data set is generated so as to have a DTI image including a T2 image and an ADC (Apparent Diffusion Coefficient) image. To clarify the positional relation between the nerve fiber bundle and the tumor and accurately execute an operation plan, the figure expressing the tumor is accurately extracted from the DTI image obtained as described above by segmentation. After that, by using the extraction image including the figure expressing the tumor, fusion display is performed. For example, noise is eliminated from the DTI image by using an anisotropic diffusion filter (refer to, for example, non-patent document 1), a figure expressing a tumor is extracted by segmentation according to, for example, the fast marching level set method (refer to, for example, non-patent document 2), and fusion display is performed with the extraction image obtained by extracting the figure expressing the tumor by segmentation.

In the DTI image obtained, however, the pixel values of the figure expressing the tumor and those of a cerebral ventricle filled with CSF are almost the same. When the tumor and the cerebral ventricle are close to each other or in contact with each other, in some cases, their figures are extracted from the DTI image in a state where the plural figures showing the tumor and the cerebral ventricle are connected to each other. Therefore, at the time of performing the fusion display by using the extraction image, not only the figure expressing the tumor but also the other figures of the cerebral ventricle and the like are included in the extraction image. There are cases such that it is difficult for the operator who observes the fusion-displayed image to clearly grasp the positional relation between a nerve fiber bundle and a tumor and appropriately execute an operation plan.

Consequently, methods of solving the problem by executing imaging processes on the DTI image have been proposed.

Concretely, a method of generating an extraction image in which only a tumor is extracted has been proposed, by preliminarily scanning the head with a pulse sequence of the FLAIR (fluid attenuated IR) method, generating an image in which contrast occurs between a cerebral ventricle and a tumor, obtaining the positional information of pixels corresponding only to the cerebral ventricle and, after that, performing an imaging process of masking the pixel portion corresponding to the cerebral ventricle in the DTI image obtained as described above (refer to, for example, non-patent document 3).

In another method, a segmentation process is executed on a DTI image having a connection figure including a plurality of figures connected to each other to selectively extract the connection figure. After that, by sequentially performing erosion (reducing) process and dilation (expanding) process in the morphologic operation, the connection figure is divided into a figure of a tumor and a figure of a cerebral ventricle. After that, a segmentation of only the figure expressing the tumor is performed from the image having the separated figures (refer to, for example, non-patent document 4).

Non-patent document 1. G. Gerig et. A1, IEEE trans Med. Imaging, 11(2), 221-232, 1992.
Non-patent document 2. J. A. Sethian, Level set method and fast marching method, Cambridge University Press, 1999.
Non-patent document 3. S. Saraswathy et. A1, ISMRM 2006, p. 1609.
Non-patent document 4. Toriwaki et. A1, Image Information Process (1), pp. 73-76, Corona Publishing Co., Ltd. 2005.

In the former case, however, it is necessary to perform a scan with a pulse sequence of the FLAIR method or the like in addition to a scan for generating a DTI image. Consequently, time required for the scans is long and, in some cases, diagnosis cannot be efficiently conducted.

In the latter case, in some cases, a part of the topology of the tumor in the DTI image is lost due to execution of the erosion process and the dilation process in the morphological operation. That is, there is the case that the shape of the tumor in the DTI image and that in an image obtained after the erosion process and the dilation process differ from each other. In this case, it is not easy to appropriately extract only the tumor, and diagnosis cannot be efficiently conducted.

As described above, it is difficult to obtain an extraction image by properly and efficiently extracting a figure to be extracted from an original image having a connection figure in which a plurality of figures of, for example, a tumor and a cerebral ventricle in the DTI image are connected to each other.

SUMMARY OF THE INVENTION

It is desirable that the problems described previously are solved.

One aspect of the invention provides an image processing apparatus for performing an imaging process on an original image having a connection figure including a first figure and a second figure connected to the first figure to generate an extraction image of the first figure extracted, including: a first image processor for obtaining a first image in which the connection figure in the original image is selectively extracted by performing a segmentation process on the original image; a second image processor for obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained by the first image processor; a third image processor for obtaining a third image by performing a segmentation process so as to selectively extract the third figure in the second image obtained by the second image processor; a fourth image processor for obtaining a fourth image by performing a process of obtaining the difference between the first image obtained by the first image processor and the third image obtained by the third image processor; a fifth image processor for obtaining a fifth image by determining whether the size of a figure included in the fourth image obtained by the fourth image processor is equal to or larger than a reference value, and when the size is equal to or larger than the reference value, eliminating the figure from the fourth image and, when the size is less than the reference value, processing the fourth image so as to leave the figure in the fourth image; and a sixth image processor for obtaining the extraction image by adding the third image obtained by the third image processor and the fifth image obtained by the fifth image processor.

Preferably, the image processing apparatus further includes a region-of-interest setting unit for setting a region of interest so as to correspond to the first figure in the original image. The third image processor selectively extracts the third figure in the second image so as to correspond to the first figure on the basis of positional information of the region of interest set in the original image by the region-of-interest setting unit.

Preferably, the region-of-interest setting unit sets the region of interest on the basis of an instruction from an operator.

Preferably, the image processing apparatus further includes a seventh image processor for executing a segmentation process on the extraction image obtained by the sixth image processor.

Preferably, an image generated on the basis of a magnetic resonance signal is used as the original image.

Preferably, an image generated on the basis of the magnetic resonance signal obtained by scanning an imaging region including a tumor in a subject and a cerebral ventricle near the tumor by diffusion tensor imaging is used as the original image. In the original image, the first figure corresponds to the tumor, and the second figure corresponds to the cerebral ventricle.

Another aspect of the invention provides an image processing method of performing an imaging process on an original image having a connection figure including a first figure and a second figure connected to the first figure to generate an extraction image of the first figure extracted, including: a first image processing step of obtaining a first image in which the connection figure in the original image is selectively extracted by performing a segmentation process on the original image; a second image processing step of obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained in the first image processing step; a third image processing step of obtaining a third image by performing a segmentation process so as to selectively extract the third figure in the second image obtained in the second image processing step; a fourth image processing step of obtaining a fourth image by performing a process of obtaining the difference between the first image obtained in the first image processing step and the third image obtained in the third image processing step; a fifth image processing step of obtaining a fifth image by determining whether the size of a figure included in the fourth image obtained in the fourth image processing step is equal to or larger than a reference value, and when the size is equal to or larger than the reference value, eliminating the figure from the fourth image and, when the size is less than the reference value, processing the fourth image so as to leave the figure in the fourth image; and a sixth image processing step of obtaining the extraction image by adding the third image obtained in the third image processing step and the fifth image obtained in the fifth image processing step.

Preferably, the image processing method further includes a region-of-interest setting step of setting a region of interest so as to correspond to the first figure in the original image. In the third image processing step, the third figure in the second image is selectively extracted so as to correspond to the first figure on the basis of positional information of the region of interest set in the original image in the region-of-interest setting step.

Preferably, in the region-of-interest setting step, the region of interest is set on the basis of an instruction from an operator.

Preferably, the image processing method further includes a seventh image processing step of executing a segmentation process on the extraction image obtained in the sixth image processing step.

Preferably, an image generated on the basis of a magnetic resonance signal is used as the original image.

Preferably, an image generated on the basis of the magnetic resonance signal obtained by scanning an imaging region including a tumor in a subject and a cerebral ventricle near the tumor by diffusion tensor imaging is used as the original image. In the original image, the first figure corresponds to the tumor, and the second figure corresponds to the cerebral ventricle.

Another aspect of the invention provides a magnetic resonance imaging apparatus for generating an original image having a connection figure including a first figure and a second figure connected to the first figure on the basis of a magnetic resonance signal obtained by scanning an imaging region in a subject, and executing imaging process on the original image, thereby generating an extraction image of the first figure extracted, including: a first image processor for obtaining a first image in which the connection figure in the original image is selectively extracted by performing a segmentation process on the original image; a second image processor for obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained by the first image processor; a third image processor for obtaining a third image by performing a segmentation process so as to selectively extract the third figure in the second image obtained by the second image processor; a fourth image processor for obtaining a fourth image by performing a process of obtaining the difference between the first image obtained by the first image processor and the third image obtained by the third image processor; a fifth image processor for obtaining a fifth image by determining whether the size of a figure included in the fourth image obtained by the fourth image processor is equal to or larger than a reference value, when the size is equal to or larger than the reference value, eliminating the figure from the fourth image and, when the size is less than the reference value, processing the fourth image so as to leave the figure in the fourth image; and a sixth image processor for obtaining the extraction image by adding the third image obtained by the third image processor and the fifth image obtained by the fifth image processor.

Preferably, the magnetic resonance imaging apparatus further includes a region-of-interest setting unit for setting a region of interest so as to correspond to the first figure in the original image. The third image processor selectively extracts the third figure in the second image so as to correspond to the first figure on the basis of positional information of the region of interest set in the original image by the region-of-interest setting unit.

Preferably, the region-of-interest setting unit sets the region of interest on the basis of an instruction from an operator.

Preferably, the magnetic resonance imaging apparatus further includes a seventh image processor for executing a segmentation process on the extraction image obtained by the sixth image processor.

Preferably, the original image is generated on the basis of the magnetic resonance signal obtained by scanning an imaging region including a tumor in a subject and a cerebral ventricle near the tumor by diffusion tensor imaging. In the original image, the first figure corresponds to the tumor, and the second figure corresponds to the cerebral ventricle.

Another aspect of the invention provides a program for making a computer perform an imaging process on an original image having a connection figure including a first figure and a second figure connected to the first figure to generate an extraction image of the first figure extracted. The program makes the computer execute: a first image processing step of obtaining a first image in which the connection figure in the original image is selectively extracted by performing a segmentation process on the original image; a second image processing step of obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained in the first image processing step; a third image processing step of obtaining a third image by performing a segmentation process so as to selectively extract the third figure in the second image obtained in the second image processing step; a fourth image processing step of obtaining a fourth image by performing a process of obtaining the difference between the first image obtained in the first image processing step and the third image obtained in the third image processing step; a fifth image processing step of obtaining a fifth image by determining whether the size of a figure included in the fourth image obtained in the fourth image processing step is equal to or larger than a reference value, when the size is equal to or larger than the reference value, eliminating the figure from the fourth image and, when the size is less than the reference value, processing the fourth image so as to leave the figure in the fourth image; and a sixth image processing step of obtaining the extraction image by adding the third image obtained in the third image processing step and the fifth image obtained in the fifth image processing step.

The invention can provide an image processing apparatus, an image processing method, a magnetic resonance imaging apparatus, and a program capable of properly and efficiently extracting a figure from an original image having a plurality of figures connected to each other.

Further objects and advantages of the present invention will be apparent from the following description of the preferred embodiments of the invention as illustrated in the accompanying drawings.

DETAILED DESCRIPTION OF THE INVENTION

An embodiment of the invention will be described hereinbelow with reference to the drawings.

Figure 1:
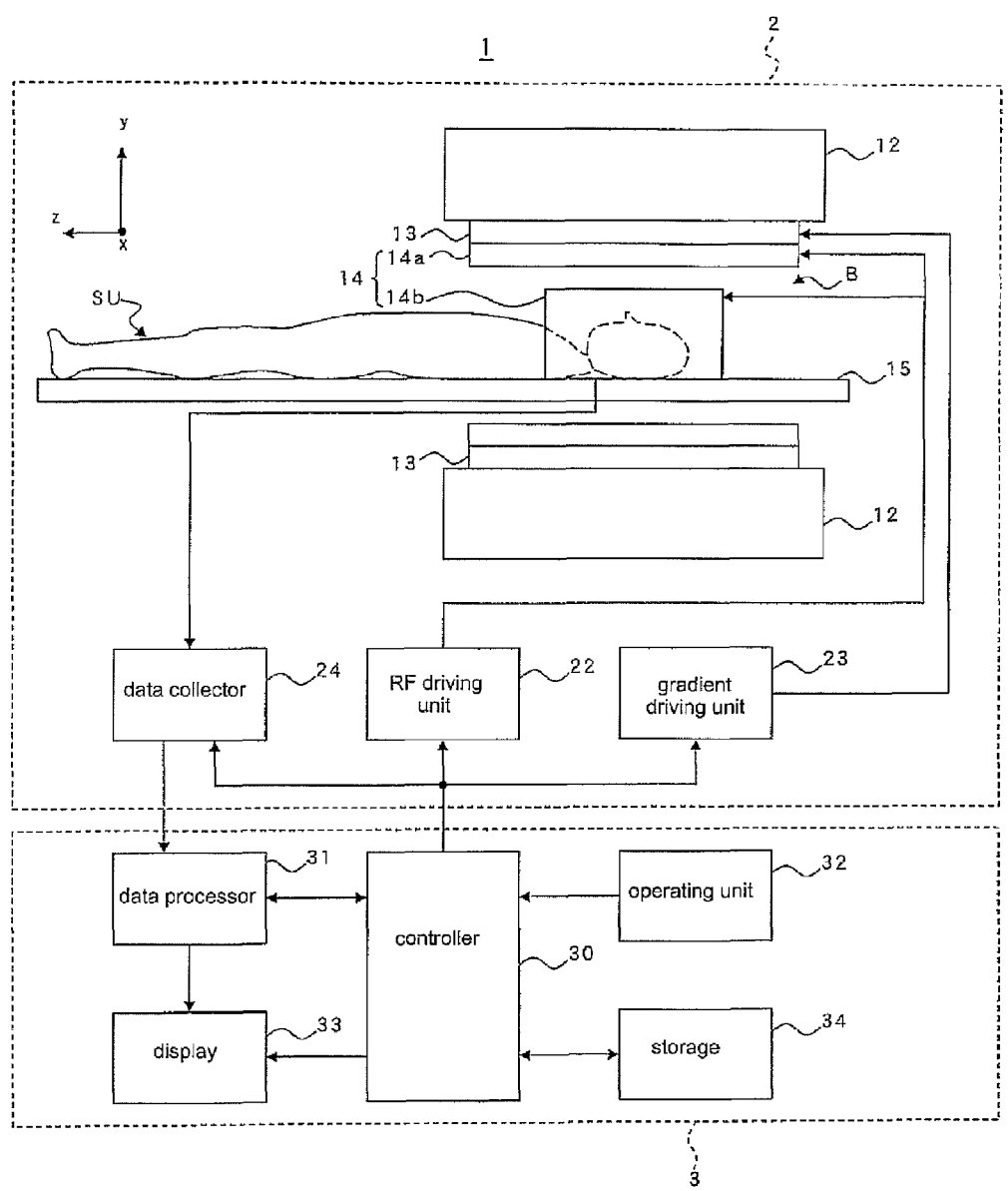
FIG. 1 is a configuration diagram showing the configuration of a magnetic resonance imaging apparatus 1 in an embodiment of the invention.

Apparatus Configuration. FIG. 1 is a configuration diagram showing the configuration of a magnetic resonance imaging apparatus 1 in an embodiment of the invention.

As shown in FIG. 1, the magnetic resonance imaging apparatus 1 of the embodiment has a scanner 2 and an operator console 3. In a static magnetic field space, the scanner 2 performs a scan by transmitting an RF pulse to an imaging region of a subject and obtaining a magnetic resonance signal generated in the imaging region to which the RF pulse was transmitted. After that, on the basis of the magnetic resonance signal obtained by performing the scan, the operator console 3 generates an image of the imaging region.

The scanner 2 will be described.

As shown in FIG. 1, the scanner 2 has a static magnetic field magnet unit 12, a gradient coil unit 13, an RF coil unit 14, a cradle 15, an RF driving unit 22, a gradient driving unit 23, and a data collector 24, and performs a scan to obtain a magnetic resonance signal generated in a subject SU. After the imaging region in the subject SU is placed in an imaging space B in which a static magnetic field is generated, the scanner 2 transmits RF pulses to the subject SU so as to excite spins in the imaging region in the subject SU and transmitting gradient pulses to the subject SU to which the RF pulses were transmitted, thereby obtaining a magnetic resonance signal generated in the subject SU.

The components of the scanner 2 will be described one by one.

The static magnetic field magnet unit 12 is constructed by, for example, a superconducting magnet (not shown), and generates static magnetic fields in the imaging space B in which the subject SU is enclosed. The static magnetic field magnet unit 12 generates static magnetic fields in the body axis direction (z direction) of the subject SU placed on the cradle 15. The static magnetic field magnet unit 12 is constructed by a pair of permanent magnets.

The gradient coil unit 13 generates gradient magnetic fields in the imaging space B in which the static magnetic fields are generated, and adds spatial position information to the magnetic resonance signal received by the RF coil unit 14. The gradient coil unit 13 is made by three systems so as to correspond to three-axis directions orthogonal to each other, which are the z direction along the static magnetic field direction, the x direction, and the y direction. They transmit gradient pulses to form gradient magnetic fields in a frequency encoding direction, a phase encoding direction, and a slice selecting direction in accordance with the imaging parameters. Concretely, the gradient coil unit 13 applies the gradient magnetic field in the direction of selecting a slice of the subject SU, and selects a slice of the subject SU excited by the RF pulses transmitted from the RF coil unit 14. The gradient coil unit 13 also applies the gradient magnetic field in the direction of encoding the phase of the subject SU to encode the phase of the magnetic resonance signal from the slice excited by the RF pulses. The gradient coil unit 13 applies the gradient magnetic field in the frequency encoding direction of the subject SU to encode the frequency of the magnetic resonance signal from the slice excited by the RF pulses.

The RF coil unit 14 transmits the RF pulses as electromagnetic waves to the imaging region in the subject SU to generate high-frequency magnetic fields in the imaging space B in which the static magnetic fields are generated by the static magnetic field magnet unit 12, and excites spins of protons in the imaging region in the subject SU. The RF coil unit 14 receives, as magnetic resonance signals, electromagnetic waves generated from protons in the imaging region in the subject SU excited. In the embodiment, as shown in FIG. 1, the RF coil unit 14 has a first RF coil 14a and a second RF coil 14b. For example, the first RF coil 14a transmits RF pulses, and the second RF coil 14b receives the magnetic resonance signal.

The cradle 15 has a table on which the subject SU is mounted. The cradle 15 moves the table between the inside and the outside of the imaging space B on the basis of a control signal from a controller 30.

The RF driving unit 22 drives the RF coil unit 14 to transmit RF pulses to the inside of the imaging space B so that the high-frequency magnetic field is generated in the imaging space B. On the basis of a control signal from the controller 30, the RF driving unit 22 modulates a signal from an RF oscillator (not shown) by using a gate modulator (not shown) to a predetermined envelope signal at a predetermined timing. After that, the RF driving unit 22 amplifies the signal modulated by the gate modulator by an RF power amplifier (not shown), outputs the amplified signal to the RF coil unit 14, and transmits an RF pulse.

The gradient driving unit 23 drives the gradient coil unit 13 on the basis of the control signal from the controller 30 to generate gradient magnetic fields in the imaging space B in which the static magnetic fields are generated. The gradient driving unit 23 has driving circuits (not shown) of three systems in correspondence with the gradient coil unit 13 of three systems.

The data collector 24 collects the magnetic resonance signal received by the RF coil unit 14 on the basis of the control signal from the controller 30. In the data collector 24, a phase detector (not shown) performs phase detection on the magnetic resonance signal received by the RF coil unit 14 by using an output of an RF oscillator (not shown) of the RF driving unit 22 as a reference signal. After that, by using an A/D converter (not shown), the magnetic resonance signal as an analog signal is converted to a digital signal, and the digital signal is output.

The operator console 3 will be described.

The operator console 3 has, as shown in FIG. 1, the controller 30, a data processor 31, an operating unit 32, a display 33, and a storage 34.

The components of the operator console 3 will be described one by one.

The controller 30 has a computer and a memory storing a program for making the computer execute a predetermined data process, and controls the other components. To the controller 30, operation data from the operating unit 32 is input. On the basis of the operation data input from the operating unit 32, the controller 30 outputs control signals to the RF driving unit 22, the gradient driving unit 23, and the data collector 24 to execute a predetermined scan. The controller 30 also performs a control by outputting control signals to the data processor 31, the display 33, and the storage 34.

The data processor 31 has a computer and a memory storing a program for making the computer execute a predetermined data process, and executes data process on the basis of the control signal from the controller 30. Concretely, the data processor 31 generates an image of the imaging region on the basis of the magnetic resonance signal obtained by scanning the imaging region in the subject by the scanner 2 and, after that, outputs the generated image to the display 33.

In the embodiment, the data processor 31 generates a DTI (Diffusion Tensor Imaging) image on the basis of a magnetic resonance signal obtained by scanning, with the scanner 2, a head portion including a tumor and a cerebral ventricle near the tumor in the subject, as the imaging region, by DTI. In the DTI image, a first figure showing a tumor and a second figure showing the cerebral ventricle near the tumor are displayed including a connected figure of the first and second figures, which is generated because the figures are made of pixel values similar to each other. After that, by executing imaging process using the DTI image as the original image, an extraction image obtained by extracting the first figure showing the tumor is generated. The data processor 31 generates a fusion image for performing fusion display to clarify the positional relation between the nerve fiber bundle and the tumor by using the extraction image obtained by extracting the first figure showing the tumor.

Figure 2:
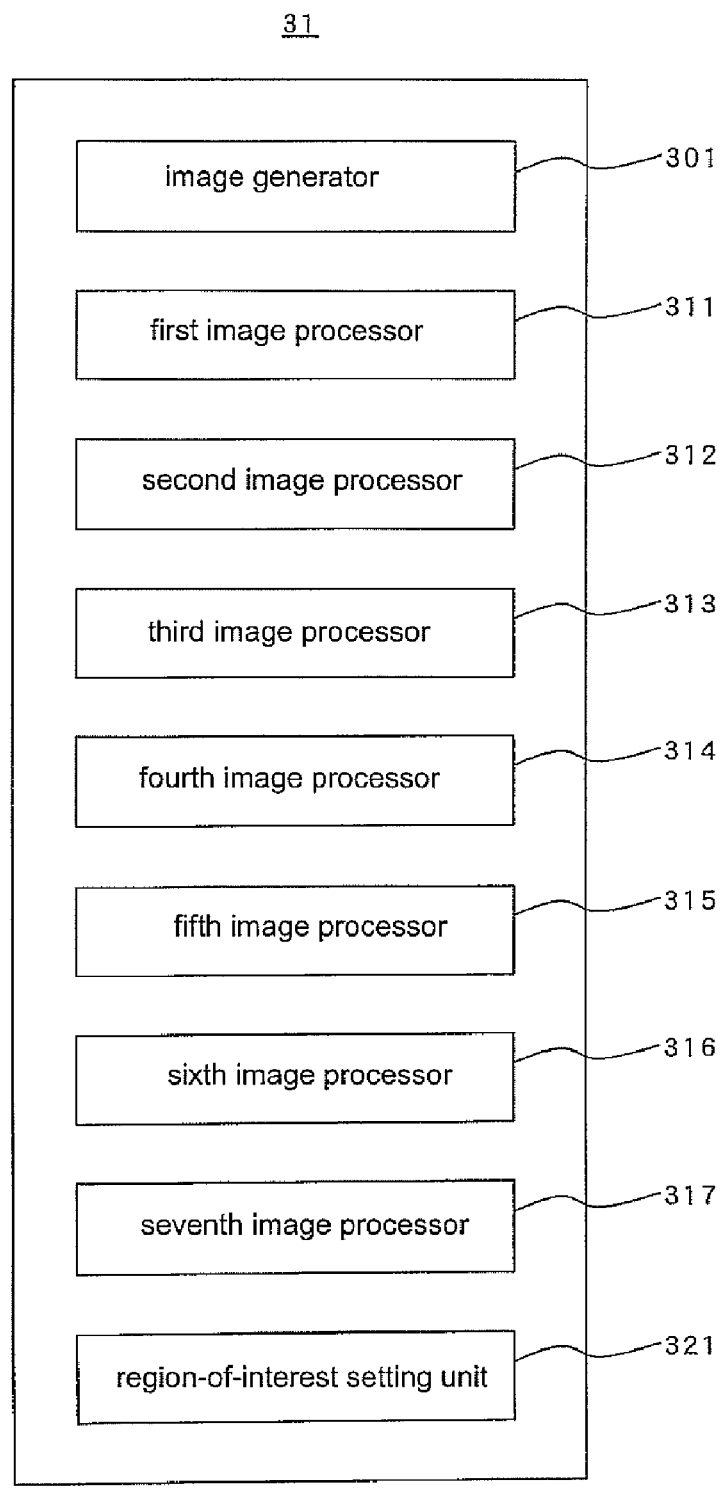
FIG. 2 is a block diagram showing main components of a data processor 31 in an embodiment of the invention.

FIG. 2 is a block diagram showing main components of the data processor 31 in the embodiment of the invention. FIGS. 3A to 3D are diagrams conceptually showing images subjected to imaging processes in the components in order to describe the imaging processes executed by the components of the data processor 31 in the embodiment of the invention.

FIGS. 4E to 4H are diagrams conceptually showing images subjected to the imaging processes in the components in order to describe the imaging processes executed by the components of the data processor 31 subsequent to the processes in FIGS. 3A to 3D in the embodiment of the invention.

As shown in FIG. 2, the data processor 31 has an image generator 301, a first image processor 311, a second image processor 312, a third image processor 313, a fourth image processor 314, a fifth image processor 315, a sixth image processor 316, a seventh image processor 317, and a region-of-interest setting unit 321. The components are realized when the computer is made function as will be described later by a program, perform imaging processes on an original image having a connected figure including a plurality of figures connected to each other to extract a figure to be extracted in the connected figure, thereby generating an extracted image including the figure to be extracted. For example, by extracting the figure showing the tumor, the extraction image is generated.

The components of the data processor 31 will be described.

The image generator 301 of the data processor 31 uses the magnetic resonance signal obtained by the scanning of the scanner 2 as raw data and generates a digital image of the imaging region in the subject SU. In the embodiment, as described above, a DTI data set is generated on the basis of the magnetic resonance signal obtained by scanning the head of the subject by the DTI. For example, as the DTI data set, a DTI image including a T2 image and an ADC image is generated. As the details will be described later, the DTI image includes a plurality of figures showing a tumor and a cerebral ventricle near the tumor. Since the plurality of figures are close to each other and are made of similar pixel values, a connection figure in which those figures are connected to each other appears. The DTI image is displayed on the display screen of the display 33. By the operator observing the original image displayed, the positional information of a region of interest is input to the operating unit 32 so as to set the region of interest in correspondence with the figure showing the tumor to be extracted from the connection figure. After that, in the connection figure in the DTI image, the region of interest is set so as to correspond to the figure showing the tumor by the region-of-interest setting unit 321.

Figure 3:
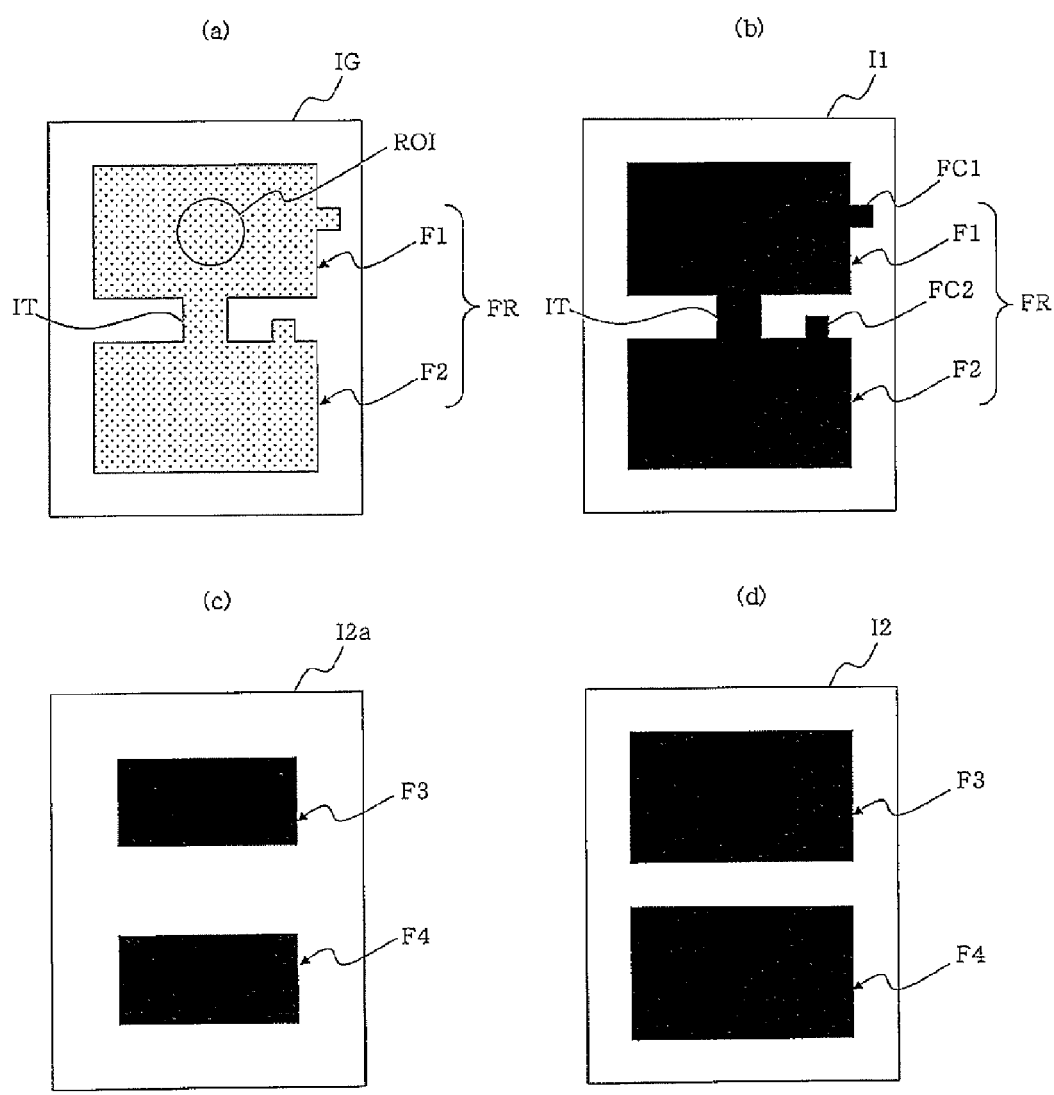
FIGS. 3A, 3B, 3C, and 3D are diagrams conceptually showing images subjected to imaging processes in the components in order to describe the imaging processes executed by the components of the data processor 31 in the embodiment of the invention.

FIG. 3A is a diagram conceptually showing an original image IG generated by the image generator 301 and to be subjected to the imaging processes in the components in order to describe the image processes of the components.

As shown in FIG. 3A, the original image IG generated by the image generator 301 includes a plurality of figures of a first figure F1 and a second figure F2 close to the first figure F1. The first and second figures F1 and F2 are connected to each other via a connection part IT and are displayed as a connection figure FR. As shown in FIG. 3A, in the original image IG, a region of interest is set by the region-of-interest setting unit 321 so as to correspond to the first figure F1 to be extracted in the connection figure FR in which a plurality of figures are connected, and a region-of-interest display image ROI showing the region of interest is displayed. After that, the original image IG is sequentially subjected to the imaging processes in the first to seventh image processors 311 to 317, thereby extracting the first figure F1.

The first image processor 311 in the data processor 31 performs a segmentation process on the DTI image as the original image including the connection figure formed by the image generator 301 to thereby obtain, as a first image, the connection figure selectively extracted from the original image. In the embodiment, though details are described later, the segmentation process according to, for example, the fast marching level set method is performed on one of the T2 image and the ADC image obtained as the DTI image. Concretely, in the connection figure in the DTI image, an average value of pixel values, standard deviation, and the like of pixels in the region of interest set by the region-of-interest setting unit 321 so as to correspond to the first figure showing the tumor are calculated as feature amounts of the tumor. After that, on the basis of the feature amounts of the tumor, the segmentation process is executed. Since the figure showing the tumor and the figure showing the cerebral ventricle have similar pixel values, when the tumor and the cerebral ventricle are close to or in contact with each other, a connection figure in which the plural figures showing the tumor and the cerebral ventricle are connected is cut from the DTI image. That is, as a result of the segmentation process, the connection figure included in the DTI image is selectively extracted, and a binary image obtained by setting the pixel values corresponding to the connection figure as "1" and setting the pixel values other than the connection figure as "0" is derived as a first image.

The segmentation process is not limited to the fast marching level set method. Other segmentation methods such as the region growing method and the active contour model method may be applied.

FIG. 3B is a diagram conceptually showing a first image I1 obtained by executing the imaging process on the original image IG by the first image processor 311.

As shown in FIG. 3B, the first image I1 is obtained in such a manner that the connection figure FR included in the original image IG shown in FIG. 3A is selectively extracted, the pixel values corresponding to the extracted connection figure FR are set as "1", and the pixel values corresponding to the other part are set as "0" (in the diagram, pixels having the pixel value "1" are displayed in "black" and pixels having the pixel value "0" are displayed in "white").

As described above, the first image processor 311 executes the segmentation process on the original image IG to selectively extract the connection figure FR from the original image IG, thereby obtaining the first image I1.

The second image processor 312 in the data processor 31 sequentially performs erosion process and dilation process in the morphologic operation so as to separate the connected first and second figures from each other in the connection figure included in the first image obtained by the first image processor 311. By the processes, the second image processor 312 generates a second image including a third figure corresponding to the first figure in the connection figure and separated from the second figure, and a fourth figure corresponding to the second figure and separated from the first figure. Specifically, an opening process in the morphological operation is executed to sequentially obtain Minkowski sum and Minkowski difference, thereby separating the connected figures from each other, in the connection figure in which the plural figures are connected to each other. As the details will be described later, in the embodiment, an image obtained by separating the first figure representing the tumor and the second figure representing the cerebral ventricle in the connection figure included in the first image to the third and fourth figures, respectively, is derived as a second image.

FIGS. 3C and 3D are diagrams conceptually showing images I2a and I2, respectively, obtained by sequentially performing the erosion process and the dilation process on the first image I1 by the second image processor 312.

As shown in FIG. 3C, by performing the erosion process on the first image I1 shown in FIG. 3B, the connection figure IR included in the first image I1 is reduced to separate the first and second figures F1 and F2 in the connection figure IR from each other to obtain the third and fourth figures F3 and F4, respectively.

Concretely, at the time of executing the erosion process, one of the pixels in the first image I1 is set as a target pixel. A process of setting the pixel value of the target pixel to "0" in the case where even one of the pixel values of the target pixel and pixels adjacent to the target pixel is "0" is sequentially performed on each of the pixels, thereby reducing the first image I1. Specifically, an adjacent-pixel pattern including the target pixel and pixels adjacent to the target pixel is sequentially moved to pixels noted as target pixels. The arithmetic process is performed in such a manner that, in the case where even one of the pixel values of the pixels in the adjacent-pixel pattern is "0", the pixel value of the target pixel is set to 0. The second image processor 312 executes the erosion process by the number of times of the erosion process entered to the operating unit 32 by the operator. By the process, as understood from comparison between FIGS. 3B and 3C, the first and second figures F1 and F2 included in the connection figure FR in the first image I1 are separated from each other. That is, a connection part IT between the first and second figures F1 and F2 disappears, and the connection figure FR is separated to the third and fourth figures F3 and F4. In addition, projections FC1 and FC2 from the first and second figures F1 and F2 disappear.

Figure 5:
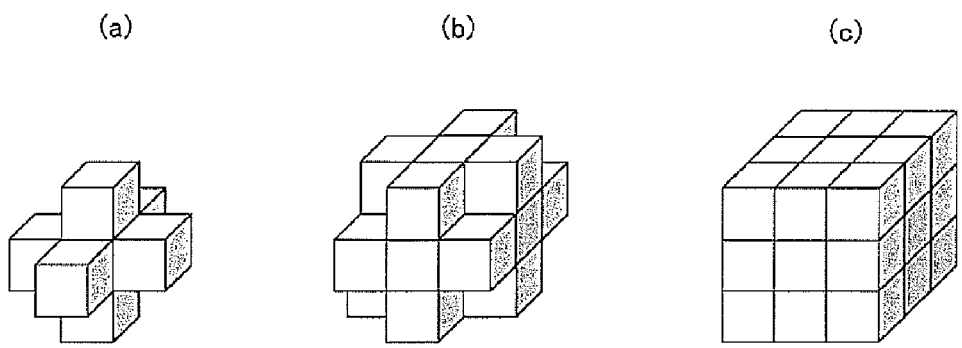
FIGS. 5A to 5C are diagrams showing adjacent-pixel patterns used at the time of executing the erosion process in the embodiment of the invention.

FIGS. 5A to 5C are diagrams showing adjacent-pixel patterns used at the time of executing the erosion process in the embodiment of the invention.

As shown in FIG. 5A, for example, when the first image I1 is a three-dimensional image, as an adjacent-pixel pattern, a 6-adjacent-pixel pattern including six pixels adjacent to the target pixel in the directions of three dimensions is used. Alternately, an 18-adjacent-pixel pattern including adjacent 18 pixels as shown in FIG. 5B, a 26-adjacent-pixel pattern including adjacent 26 pixels as shown in FIG. 5C, or the like may be used. For example, when the first image I1 is a two-dimensional image, an eight-adjacent-pixel pattern including eight pixels adjacent to a target pixel so as to surround the target pixel in a two-dimensional plane having the target pixel as a center, or the like is used.

After performing the erosion process as described above, the dilation process is performed on the image I2a subjected to the erosion process shown in FIG. 3C so as to be dilated, thereby obtaining the second image I2 as shown in FIG. 3D.

Concretely, at the time of performing the dilation process, one of the pixels constructing the first image I1 is set as a target pixel. A process of setting the pixel value of the target pixel to "1" in the case where even one of the pixel values of the target pixel and pixels adjacent to the target pixel is "1" is sequentially performed on each of the pixels, thereby dilating the first image I1. Specifically, an adjacent-pixel pattern including the target pixel and pixels adjacent to the target pixel is sequentially moved to pixels noted as target pixels. The arithmetic process is performed in such a manner that, in the case where even one of the pixel values of the pixels in the adjacent-pixel pattern is "1", the pixel value of the target pixel is set to 1. By using an adjacent-pixel pattern similar to, for example, any of the adjacent-pixel patterns shown in FIGS. 5A to 5C used for the erosion process, the dilation process is executed. The second image processor 312 executes the dilation process by the same number as the number of times of the erosion process entered to the operating unit 32 by the operator. By the process, as shown in FIG. 3D, the reduced third and fourth figures F3 and F4 are dilated in a state where they are separated from each other in a manner similar to the first image I1. The second image I2 is generated so as to include the third figure F3 corresponding to the first figure F1 and the fourth figure F4 corresponding to the second figure F2.

In such a manner, the second image processor 312 sequentially performs the erosion process and the dilation process in the morphologic operation on the first image I1. By separating the plural figures F1 and F2 connected to each other via the connection figure FR included in the first image I1, the second image I2 including the plural figures F3 and F4 separated from each other is obtained.

The third image processor 313 in the data processor 31 performs a segmentation process on the second image obtained by the second image processor 312 so as to selectively extract a third image corresponding to the first image to be extracted in the connection figure in the second image, thereby obtaining the third image. In the embodiment, the segmentation process is executed by using, for example, the region growing method. Specifically, the third image processor 313 selectively extracts the third figure in the second image so as to correspond to the first figure on the basis of the positional information in which the region of interest is set in the DTI image as the original image by the region-of-interest setting unit 321. Concretely, when the region of interest is set so as to correspond to the first figure showing the tumor in the connection figure included in the DTI image as the original image, on the basis of the positional information of the set region of interest, a third figure corresponding to the tumor is cut from the second image including the third figure corresponding to the set region of interest and the fourth figure corresponding to the cerebral ventricle close to the region of interest, thereby obtaining the third image.

Figure 4:
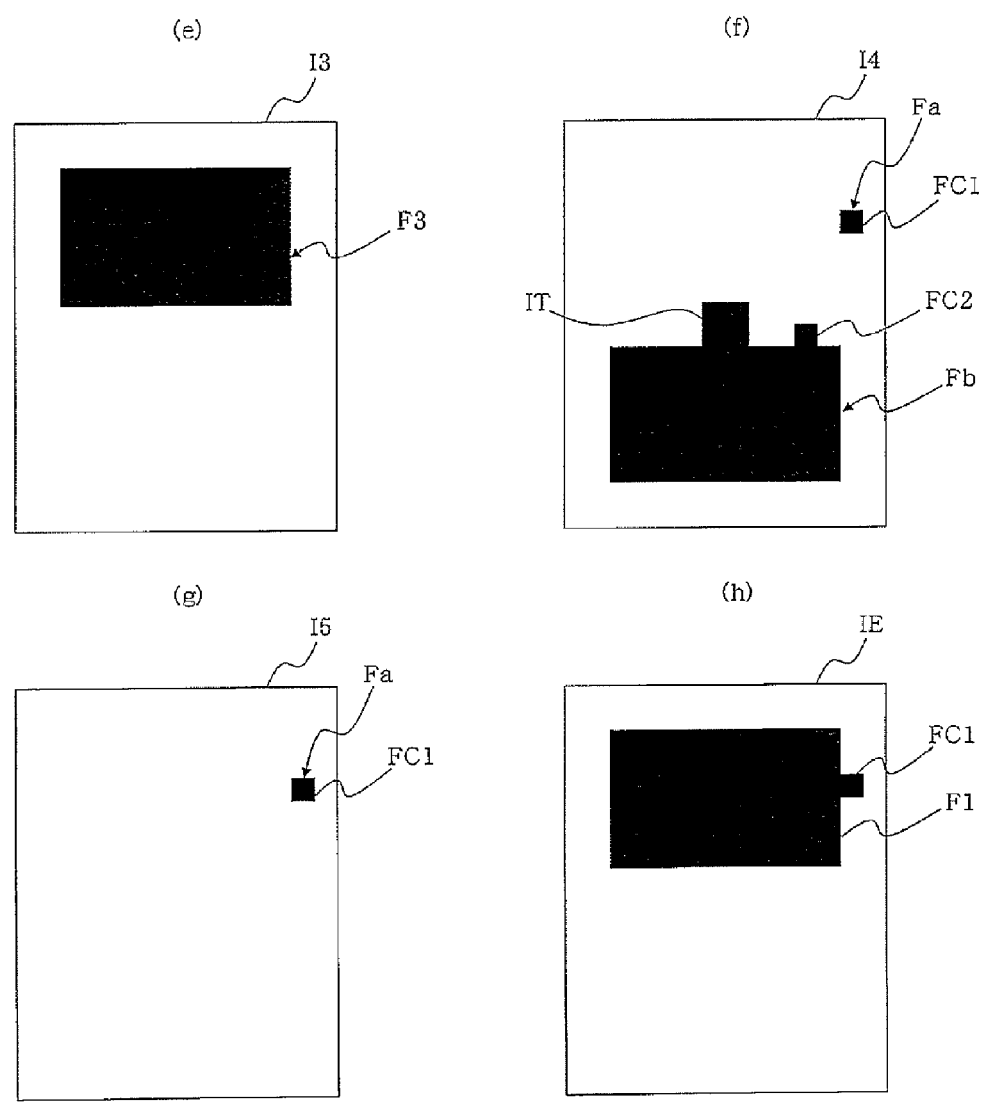
FIGS. 4E, 4F, 4G, and 4H are diagrams conceptually showing images subjected to the imaging processes in the components in order to describe the imaging processes executed by the components of the data processor 31 subsequent to the processes in FIGS. 3A, 3B, 3C, and 3D in the embodiment of the invention.

FIG. 4E is a diagram conceptually showing a third image I3 obtained by executing the imaging process on the second image I2 by the third image processor 313.

As shown in FIG. 4E, by performing the segmentation process so as to selectively extract the third figure F3 on the second image I2 shown in FIG. 3D, the third image I3 is obtained. As described above, on the basis of the positional information of the set region of interest ROI in the original image IG, the third figure F3 in the second image I2 is selectively extracted so as to correspond to the first figure F1, thereby obtaining the third image I3. In the third image I3, by the erosion process and the dilation process in the morphologic operation, the third figure F3 in which a part of the topology of the first figure F1 is lost is extracted. Consequently, the fourth, fifth, and sixth image processes 314, 315, and 316 sequentially execute imaging processes to reconstruct the lost topology.

As described above, the third image processor 313 performs the segmentation process on the second image I2 to selectively extract the figure F3 corresponding to the figure F1 to be extracted in the connection figure FR from the second image I2, thereby obtaining the third image I3.

The fourth image processor 314 in the data processor 31 performs a differencing process on the first image obtained by the first image processor 311 and the third image obtained by the third image processor 313 to thereby obtain a fourth image.

FIG. 4F is a diagram conceptually showing a fourth image I4 obtained by performing an imaging process on the third image I3 by the fourth image processor 314.

As shown in FIG. 4F, at the time of obtaining the fourth image I4, the differencing process is performed on pixel values of pixels in corresponding positions in the first image I1 shown in FIG. 3B and the third image I3 shown in FIG. 4E to calculate the difference value of each of the pixels. By disposing the difference values so as to correspond to the pixel positions, the fourth image I4 is generated. That is, by performing the differencing process on the pixel values of the first image I1 including the first figure F1 whose topology is not lost and the third image I3 including the third figure F3 obtained by loosing a part of the topology of the first figure F1, the fourth image I4 including the information of the lost topology in the third image I3 is generated. Consequently, the fourth image I4 generated here includes a plurality of figures Fa and Fb having the projections FC1 and FC2 projected from the first and second figures F1 and F2, respectively.

In such a manner, the fourth image processor 314 obtains the fourth image I4 by executing the differencing process between the first image I1 and the third image I3.

The fifth image processor 315 in the data processor 31 executes a process of eliminating the figure included in the fourth image obtained by the fourth image processor 314 from the fourth image on the basis of the size of the figure, thereby obtaining a fifth image. The fifth image processor 315 determines whether the size of the figure included in the fourth image obtained by the fourth image processor 314 is equal to or larger than a reference value or not. When the size of the figure is equal to or larger than the reference value, the fifth image processor 315 eliminates the figure from the fourth image. When the size of the figure is smaller than the reference value, the figure is left in the fourth image. As a result of the process, a fifth image is obtained. As the details will be described later, the fifth image is obtained as an image showing the information of the lost topology.

FIG. 4G is a diagram conceptually showing a fifth image I5 obtained by executing the imaging process on the fourth image I4 by the fifth image processor 315.

As shown in FIG. 4G, at the time of obtaining the fifth image I5, the area of each of the plurality of figures Fa and Fb included in the fourth image I4 shown in FIG. 4F is calculated. On the basis of the values of the calculated areas, a process of eliminating the figure included in the fourth image I4 is executed. For example, a part in which pixels whose pixel values are "1" are continued in the adjacent pixels is determined as a figure, and the number of pixels constructing the figure is calculated as the area of the figure. Whether the area of each of the plural figures included in the fourth image I4 is equal to or larger than a predetermined reference number or not is determined. When the area of the figure is equal to or larger than the reference value, the figure whose area is equal to or larger than the reference value is eliminated from the fourth image I4. When the area of the figure is less than the reference value, the figure whose area is less than the reference value is left in the fourth image I4. By the process performed on the fourth image I4, the fifth image I5 is obtained. That is, when the value of the area is smaller than the predetermined reference value, the figure is determined as the figure showing the lost topology. As the image showing the lost topology, the fifth image I5 is obtained. As shown in FIG. 4G, the figure Fa which has disappeared from the first figure F1 remains, and the figure Fb corresponding to the second figure F2 is eliminated.

As described above, the fifth image processor 315 determines whether the size of each of the figures included in the fourth image I4 is equal to or larger than the reference value or not. When the size of the figure is equal to or larger than the reference value, the figure is eliminated from the fourth image I4. When the size of the figure is less than the reference value, the figure is left in the fourth image I4. By the process, the fifth image I5 is obtained.

The sixth image processor 316 in the data processor 31 adds the third image obtained by the third image processor 313 and the fifth image obtained by the fifth image processor 315, thereby obtaining an extraction image of the first figure showing the tumor in the DTI image.

FIG. 4H is a diagram conceptually showing an extraction image IE obtained by executing the imaging process on the fifth image I5 by the sixth image processor 316.

As shown in FIG. 4H, at the time of obtaining the extraction image IE, an arithmetic process is executed by adding the pixel values of corresponding pixels in the third image I3 shown in FIG. 4E and the fifth image I5 shown in FIG. 4G to calculate an addition value of each of the pixels, thereby obtaining the extraction image IE. That is, by adding the fifth image I5 including the figure showing the lost topology to the third image I3 including the third figure F3 which has lost a part of the topology of the first figure F1, the extraction image IE of the first figure F1 from which topology is not lost is generated. As a result, the extraction image IE of the first figure F1 extracted from the original image IG is obtained as shown in FIG. 4H.

As described above, the sixth image processor 316 obtains the extraction image IE by executing the process of adding the third and fifth images I3 and I5.

The seventh image processor 317 in the data processor 31 executes the segmentation process on the extraction image obtained by the sixth image processor 316. As the details will be described later, in the embodiment, the segmentation process according to, for example, the fast marching level set method is performed on the extraction image.

The region-of-interest setting unit 321 in the data processor 31 sets the region of interest so as to correspond to the first figure showing the tumor in the DTI image generated as the original image by the image generator 301. In the embodiment, the region-of-interest setting unit 321 sets the region of interest on the basis of an instruction from the operator entered to the operating unit 32.

The other components of the operator console 3 will be described.

The operating unit 32 is constructed by operating devices such as a keyboard and a pointing device. The operating unit 32 receives operation data from the operator and outputs the operation data to the controller 30, data processor 31, display 33, and storage 34. In the embodiment, the number of times of each of the erosion process and the dilation process executed by the second image processor 312 in the data processor 31 is input to the operating unit 32 by the operator. The operating unit 32 outputs operation data indicating the number of times of the erosion process and the dilation process to the data processor 31. The position of the region of interest set by the region-of-interest setting unit 321 in the data processor 31 is input to the operating unit 32 by the operator, and the operating unit 32 outputs operation data for setting the region of interest in the DTI image to the data processor 31.

The display 33 is constructed by a display device such as a CRT and displays an image on a display screen on the basis of the control signal from the controller 30. For example, the display 33 displays, on the display screen, a plurality of input images indicative of input items of operation data which is input to the operating unit 32 by the operator. The display 33 receives data of an image of the imaging region in the subject SU generated by the data processor 31 on the basis of the magnetic resonance signal from the subject SU, and displays the image on the display screen. In the embodiment, the display 33 displays a fusion image generated on the basis of the extraction image generated by the data processor 31.

The storage 34 is constructed by a memory and stores various data. The data stored in the storage 34 is accessed by the controller 30, the data processor 31, and the display 33 as necessary.

Operation. The operation for generating an image of an imaging region in the subject SU by the magnetic resonance imaging apparatus 1 of the embodiment according to the invention will now be described. The operation is executed by using a program for making the computer execute the following steps.

Figure 6:
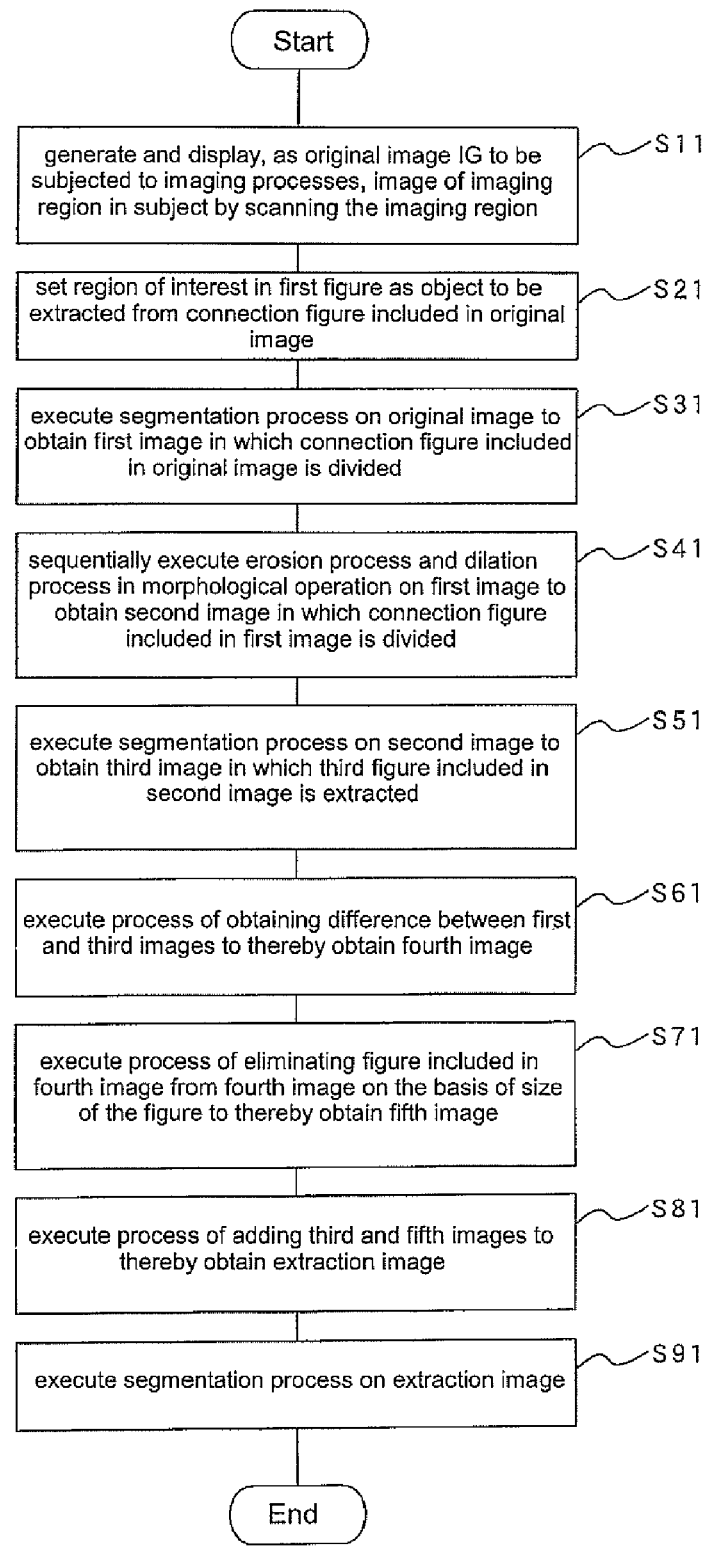
FIG. 6 is a flowchart showing operations for generating an extraction image by executing an imaging process on the original image in the embodiment of the invention.

FIG. 6 is a flowchart showing operations for generating an extraction image by executing an imaging process on the original image in the embodiment of the invention. FIGS. 7A to 7E are diagrams showing images sequentially obtained by steps of executing the imaging processes on the original image and generating the extraction image in the embodiment of the invention. FIGS. 8F to 8I are diagrams showing images sequentially obtained in the steps of generating an extraction image by executing the imaging processes on the original image, subsequent to FIGS. 7A to 7E in the embodiment of the invention.

As shown in FIG. 6, first, by scanning the imaging region in the subject, an image of the imaging region is generated and displayed as the original image IG to be subjected to the imaging processes (S11).

In this case, for example, a three-dimensional region including a diffusion anisotropic structure like brain in the head of the subject is set as the imaging region. The scanner 2 scans the imaging region by the DTI method in the imaging space B in which the static magnetic fields are generated, and a magnetic resonance signal of the imaging region is collected. On the basis of the collected magnetic resonance signal, the image generator 301 in the data processor 31 in the operator console 3 reconstructs the image of the imaging region. After that, the display 33 displays the generated image on the display screen.

In the embodiment, a slice to be obtained and the number of slices in the imaging region as the three-dimensional image are set. After that, for example, by the spin echo method, the imaging region is scanned so as to correspond to both of a pulse sequence in which MPG (Motion Probing Gradients) pulses of the same magnitude are disposed symmetrically with respect to the 180° pulse as a re-conversion pulse as a center so as to be applied in, for example, six ways and a pulse sequence in which no MPG pulses are disposed. By the scan, magnetic resonance signals of slices are collected in accordance with a combination of the MPG pulses disposed.

On the basis of the collected magnetic resonance signals, for example, a DTI image including the T2 image and the ADC image is generated as an original image. In this case, a noise eliminating process is performed with an anisotropic diffusion filter. After that, a linear interpolating process is performed in the slice direction so as to obtain isotropic voxels. By the process, the number of slices is increased to, for example, 2.5 times. The display 33 displays, on the display screen, the generated DTI image as the original image IG to be subjected to the imaging process in the following step.

Figure 7:
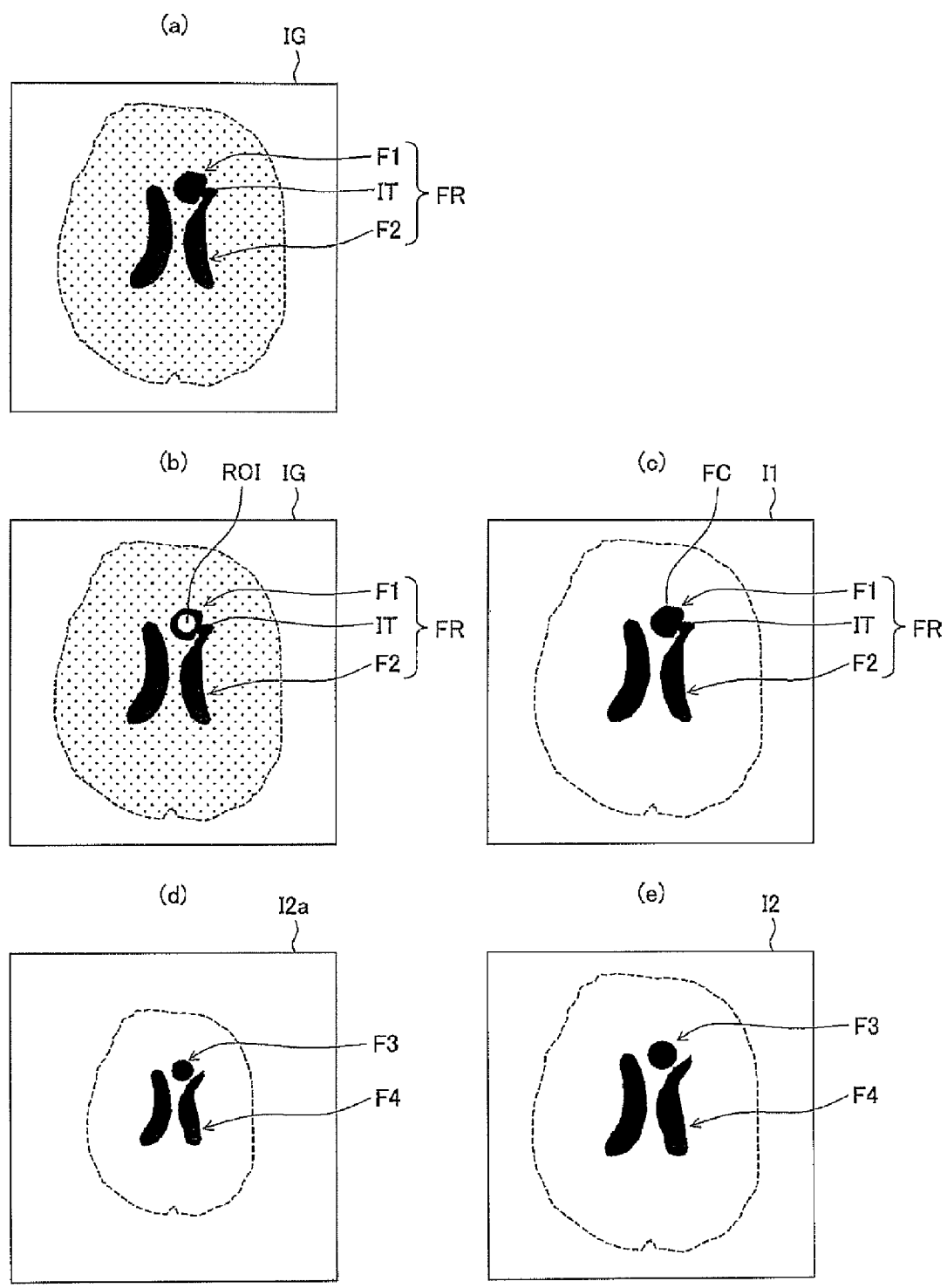
FIGS. 7A, 7B, 7C, 7D, and 7E are diagrams showing images sequentially obtained by steps of executing the imaging processes on the original image and generating the extraction image in the embodiment of the invention.

FIG. 7A is a diagram showing the original image IG generated in the step and to be subjected to the imaging process in the following step.

As shown in FIG. 7A, the original image IG as the DTI image includes the first figure F1 expressing the tumor and the second figure F2 expressing the cerebral ventricle close to the tumor. Since the plural figures such as the first and second figures F1 and F2 are close to each other and have similar pixel values, the connection figure FR in which the figures are connected via the connection part IT is displayed in the original image IG.

Next, as shown in FIG. 6, a region of interest is set in the first figure to be extracted from the connection figure included in the original image (S21).

In the embodiment, the operator observing the original image displayed as described above enters the positional information of the region of interest so as to correspond to the first figure to be extracted in the connection figure by using a pointing device or the like. After that, the region-of-interest setting unit 321 sets the region of interest so as to correspond to the first figure in the connection figure of the original image.

FIG. 7B is a diagram showing a state where the region of interest is set in the original image IG in the step.

As shown in FIG. 7B, the region of interest ROI is set so as to correspond to the first figure F1 expressing the tumor in the connection figure FR in which the first figure F1 and the second figure F2 are connected to each other via the connection part IT in the original image IG displayed. The image showing the set region of interest ROI is displayed so as to be overlaid the original image IG.

Next, as shown in FIG. 6, the segmentation process is performed on the original image, thereby obtaining the first image in which the connection figure included in the original image is divided (S31).

In the embodiment, the first image processor 311 performs the segmentation process as an imaging process on the original image, thereby obtaining a first image.

FIG. 7C is a diagram showing the first image I1 obtained in the step.

As shown in FIG. 7C, at the time of obtaining the first image I1, the connection figure FR is selectively extracted from the original image IG shown in FIG. 7A.

In the embodiment, a segmentation process according to, for example, the fat marching level set method is executed on one of the T2 image and the ADC image obtained as the DTI image which is the original image IG. As shown in FIG. 7A, an average value of pixel values, standard deviation, and the like of pixels in the region of interest ROI set so as to correspond to the first figure F1 showing the tumor to be extracted are calculated as feature amounts of the figure of the tumor to be extracted. After that, on the basis of the feature amounts of the tumor, the segmentation process is executed on the figure.

In this case, the connection figure FR is cut from the original image IG. In the connection figure FR, since the first figure F1 showing the tumor and the second figure F2 showing the cerebral ventricle are formed by similar pixel values and the tumor and the cerebral ventricle are close to each other, the first and second figures F1 and F2 are connected to each other as shown in FIG. 7C.

As a result, the first image I1 is obtained as digital image data which is binary data obtained by setting the pixel value of a pixel corresponding to the extracted connection figure FR as 1 and setting the pixel value of a pixel corresponding to the part other than the connection figure FR as 0.

Next, as shown in FIG. 6, the erosion process and dilation process in the morphologic operation are sequentially performed on the first image, thereby obtaining a second image in which the connection figure included in the first image is divided (S41).

The second image processor 312 sequentially executes the erosion process and the dilation process in the morphologic operation so as to separate the first and second figures connected to each other in the connection figure included in the first image. By the process, a second image including a third figure separated from the second figure, and a fourth figure separated from the first figure in the connection figure is obtained. Specifically, by performing an opening process in the morphological operation, the connection figure in the first figure showing the tumor and the second figure showing the cerebral ventricle are connected to each other is divided, and the resultant image is obtained as a second image including the third and fourth figures. For example, by an operator observing the images before and after the imaging process in the step, an instruction designating the number of times of the process is input to the operating unit 32, and the process is executed in accordance with the input instruction.

FIG. 7D is a diagram showing the image I2a obtained by executing the erosion process in the step.

As shown in FIG. 7D, by performing the erosion process on the first image I1 shown in FIG. 7C, the connection figure IR included in the first image I1 is reduced. The erosion process is executed in accordance with the number of times of the erosion process input to the operating unit 32 by the operator. By the processes, the first and second figures F1 and F2 connected to each other in the connection figure IR are separated to the third and fourth figures F3 and F4, respectively.

That is, the connection part IT between the first figure F1 expressing the tumor and second figure F2 expressing the cerebral ventricle in the connection figure FR disappears, and the connection figure FR is separated to the third figure F3 corresponding to the tumor and the fourth figure F4 corresponding to the cerebral ventricle. In addition, as shown in FIG. 7C, a projection FC from the first figure F1 disappears. As shown in FIG. 7D, the third figure F3 is formed only in the circular shape.

FIG. 7E is a diagram showing the second image I2 obtained by executing the dilation process in the step.

As shown in FIG. 7E, by executing the dilation process on the image I2a subjected to the erosion process shown in FIG. 7D, the image I2a subjected to the erosion process is dilated and, as a result, the second image I2 is obtained. In this case, the dilation process is executed by the same number of times as that of the erosion process entered to the operating unit 32 by the operator. By the process, the figures are dilated in a state where they are separated from each other so that the size of each of the reduced figures becomes similar to that in the first image I1. The second image I2 is generated so as to include the third figure F3 corresponding to the first figure F1 and the fourth figure F4 corresponding to the second figure F2.

In the second image I2 generated, the third figure F3 corresponding to the tumor and the fourth figure F4 corresponding to the cerebral ventricle are separated from each other. When the third and fourth figures F3 and F4 are compared with the first figure F1 corresponding to the tumor and the second figure F2 corresponding to the cerebral ventricle in the first image I1, a part of the morphology is lost.

Next, as shown in FIG. 6, the segmentation process is performed on the second image and a third image is obtained by extracting the third figure included in the second image (S51).

Specifically, the third image processor 313 performs a segmentation process on the second image so as to selectively extract a third figure in the second image, thereby obtaining the third image.

Figure 8:
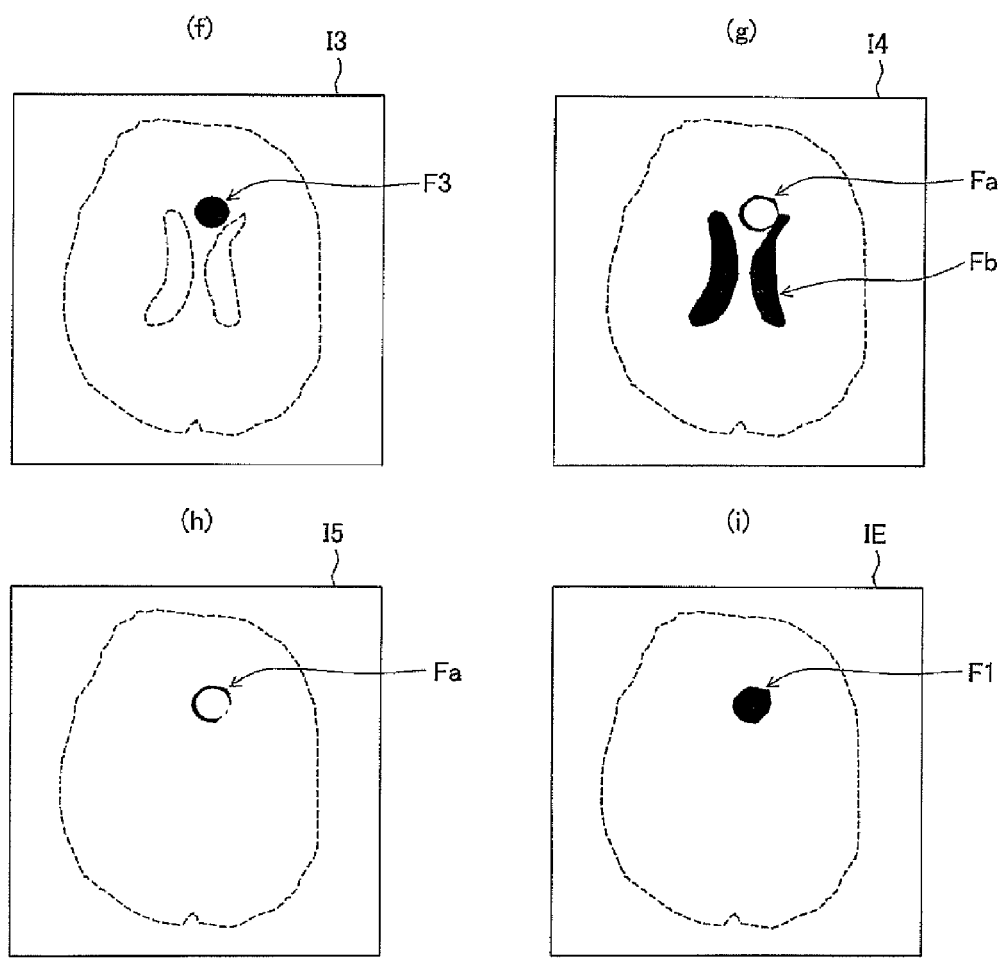
FIGS. 8F, 8G, 8H, 8I are diagrams showing images sequentially obtained in the steps of generating an extraction image by executing the imaging processes on the original image, subsequent to FIGS. 7A, 7B, 7C, 7D, and 7E in the embodiment of the invention.

FIG. 8F is a diagram showing the third image I3 obtained in the step.

As shown in FIG. 8F, at the time of obtaining the third image I3, the third figure F3 is selectively extracted from the second image I2 shown in FIG. 7E.

In the embodiment, the segmentation process is executed by using, for example, the region growing method to extract the third figure F3. Specifically, in the above-described step, as shown in FIG. 7B, the third figure F3 corresponding to the tumor is cut from the second image I2 shown in FIG. 7E on the basis of the positional information of the region of interest ROI set in correspondence with the first figure F1 expressing the tumor in the connection image FR in the original image IG. As a result, as shown in FIG. 8F, the third image I3 in which the third figure F3 is selectively extracted is obtained.

In the third image I3 generated, the third figure F3 corresponding to the tumor is properly extracted from the second image I2. When the third figure F3 is compared with the first figure F1 corresponding to the tumor in the first image I1, a part of the morphology is lost.

Next, as shown in FIG. 6, by performing the differencing process between the first and third images, a fourth image is obtained (S61).

In the embodiment, the fourth image processor 314 performs a differencing process between the first and third images obtained in the above step, thereby obtaining a fourth image.

FIG. 8G is a diagram showing the fourth image I4 obtained in this step.

As shown in FIG. 8G, at the time of obtaining the fourth image I4, the differencing process is performed on pixel values of pixels in corresponding positions in the first image I1 shown in FIG. 7C and the third image I3 shown in FIG. 8F to calculate the difference value of each of the pixels, thereby calculating the difference values of the pixels. The pixels are constructed by the difference values inn correspondence with the pixel positions.

By performing the differencing process on the pixel values of the corresponding pixels in the first image I1 including the first figure F1 whose topology is not lost and the third image I3 including the third figure F3 having the topology a part of which is lost, the fourth image I4 is generated. Consequently, the fourth image I4 includes the information of the topology lost in the third figure F3 corresponding to the tumor in the third image I3. That is, the fourth image I4 includes, as information of the lost topology in the third image I3, the projection FC projected from the first figure F1.

As shown in FIG. 6, by executing the process of eliminating the figure included in the fourth image from the fourth image on the basis of the size of the figure, a fifth image is obtained (S71).

In this case, the fifth image processor 315 executes a process of eliminating a plurality of figures constructing the fourth image from the fourth image on the basis of the size of each of the figures, thereby obtaining a fifth image.

FIG. 8H is a diagram showing the fifth image I5 obtained in the step.

As shown in FIG. 8H, at the time of obtaining the fifth image I5, first, the area of each of the plurality of figures Fa and Fb included in the fourth image I4 shown in FIG. 8G is calculated. For example, a part in which pixels whose pixel values are "1" are continued in the adjacent pixels is determined as a figure, and the number of pixels constructing the figure is calculated as the area of the figure.

After that, a process of eliminating a figure included in the fourth image I4 on the basis of the value of the calculated area is executed. Concretely, whether the calculated area of the figure in the plural figures constructing the fourth image I4 is equal to or larger than a reference value or not is determined. When the area of the figure is equal to or larger than the reference value, the figure is eliminated from the fourth image I4. On the other hand, when the area of the figure is less than the reference value, the figure is left in the fourth image I4. In such a manner, the fifth image I5 is obtained. That is, when the value of the area is smaller than the predetermined reference value, the figure is determined as the figure showing the lost topology. As the image showing the information of the lost topology, the fifth image I5 is obtained.

Next, as shown in FIG. 6, by performing the process of adding the third and fifth images, an extraction image is obtained (S81).

The sixth image processor 316 adds the third image and the fifth image, thereby obtaining an extraction image of the first figure showing the tumor in the original image.

FIG. 8I is a diagram conceptually showing an extraction image IE obtained in this step.

As shown in FIG. 8I, at the time of obtaining the extraction image IE, an arithmetic process is executed by adding the pixel values of corresponding pixels in the third image I3 shown in FIG. 8F and the fifth image I5 shown in FIG. 8H to calculate an addition value of each of the pixels. That is, the fifth image I5 including the figure showing the lost topology is added to the third image I3 including the third figure F3 which has lost a part of the topology of the first figure F1. As a result, the extraction image IE in which the first figure F1 whose topology is not lost is generated.

As shown in FIG. 6, the segmentation process is executed on the extracted image (S91).

In this case, the seventh image processor 317 executes the segmentation process on the obtained extraction image.

In the embodiment, by re-calculating the average value and the standard deviation of the pixel values of the pixels corresponding to the first figure F1 reconstructed, the segmentation process according to, for example, the fast marching level set method is performed on the extraction image. By the process, a figure to be extracted such as a tumor is properly and efficiently extracted from an original image having a connection figure in which a plurality of figures expressing, for example, a tumor and a cerebral ventricle are connected to each other, thereby obtaining an extraction image.

By using the extraction image obtained by performing the imaging processes as described above, a fusion image showing the nerve fiber bundle and the tumor is displayed. Since a figure expressing the tumor is properly and efficiently extracted and an extraction image is obtained, the positional relations between the nerve fiber bundle and the tumor are clarified in the fusion display. Consequently, an operation plan is appropriately executed.

As described above, in the embodiment, by sequentially performing the erosion process and the dilation process in the morphologic operation, a plurality of figures indicative of a tumor and a cerebral ventricle and connected to each other in a DTI image as an original image can be separated from each other. At the time of separation, even in the case where a part of the topology of the figure expressing the tumor to be extracted is lost, by executing the imaging processes, the lost part of the topology is reconstructed. Consequently, in the embodiment, an extraction image in which a figure to be extracted is extracted from an original image having a connection figure in which a plurality of figures are connected to each other can be obtained properly and efficiently. Therefore, in the embodiment, a fusion image showing the nerve fiber bundle and the tumor can be accurately displayed by using the extraction image in which an object to be extracted is properly extracted. The positional relations between the nerve fiber bundle and the tumor can be clearly grasped, and an operation plan can be executed efficiently. In particular, in the embodiment, it is unnecessary to perform a scan other than the scan for obtaining the DTI image. Consequently, the effects can be made obvious.

The magnetic resonance imaging apparatus 1 in the embodiment corresponds to the magnetic resonance imaging apparatus of the invention. The data processor 31 in the embodiment corresponds to the image processing apparatus of the invention. The first image processor 311 in the embodiment corresponds to the first image processor of the invention. The second image processor 312 in the embodiment corresponds to the second image processor of the invention. The third image processor 313 in the embodiment corresponds to the third image processor of the invention. The fourth image processor 314 in the embodiment corresponds to the fourth image processor of the invention. The fifth image processor 315 in the embodiment corresponds to the fifth image processor of the invention. The sixth image processor 316 in the embodiment corresponds to the sixth image processor of the invention. The seventh image processor 317 in the embodiment corresponds to the seventh image processor of the invention. In the embodiment, the region-of-interest setting unit 321 corresponds to the region-of-interest setting unit of the invention.

The invention is not limited to the foregoing embodiment. Various modifications made by replacing or combining specific items of each of the inventions can be employed.

For example, in the embodiment, the case where the number of times of executing the erosion process and the dilation process in the morphologic operation is set and executed on the basis of an instruction entered by the operator is described. However, the invention is not limited to the case. It is also possible to, for example, determine a predetermined reference in advance, and the number of processes may be automatically set.

Although the imaging processes in the embodiment are executed using, as the original image, the DTI image of the head of the subject generated on the basis of the magnetic resonance signal, the invention is not limited to the embodiment. For example, the invention may be applied to an image of another region in a subject. The invention may be also applied to an image generated by using, as raw data, projection data obtained by performing a scan by an X-ray CT apparatus, an echo signal obtained by a scan of an ultrasonic image diagnosing apparatus, or the like.

Although the case of obtaining an extraction image and, after that, executing the segmentation process again on the extraction image has been described, the invention is not limited to the case. For example, the segmentation process is not executed on the extraction image.

Many widely different embodiments of the invention may be configured without departing from the spirit and the scope of the present invention. It should be understood that the present invention is not limited to the specific embodiments described in the specification, except as defined in the appended claims.

The invention claimed is:

1. An image processing apparatus for performing an imaging process on an original image having a connection figure including a first figure and a second figure connected to the first figure to generate an extraction image of the first figure extracted, said image processing apparatus comprising:

a first image processor for obtaining a first image in which the connection figure in the original image is selectively extracted by performing a segmentation process on the original image;

a second image processor for obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained by the first image processor;

a third image processor for obtaining a third image by performing a segmentation process so as to selectively extract the third figure in the second image obtained by the second image processor;
a fourth image processor for obtaining a fourth image by performing a process of obtaining the difference between the first image obtained by the first image processor and the third image obtained by the third image processor;
a fifth image processor for obtaining a fifth image by determining whether the size of a figure included in the fourth image obtained by the fourth image processor is equal to or larger than a reference value, and when the size is equal to or larger than the reference value, eliminating the figure from the fourth image and, when the size is less than the reference value, processing the fourth image so as to leave the figure in the fourth image; and
a sixth image processor for obtaining the extraction image by adding the third image obtained by the third image processor and the fifth image obtained by the fifth image processor.

2. The image processing apparatus according to claim 1, further comprising a region-of-interest setting unit for setting a region of interest so as to correspond to the first figure in the original image,
wherein the third image processor selectively extracts the third figure in the second image so as to correspond to the first figure on the basis of positional information of the region of interest set in the original image by the region-of-interest setting unit.

3. The image processing apparatus according to claim 2, wherein the region-of-interest setting unit sets the region of interest on the basis of an instruction from an operator.

4. The image processing apparatus according to claim 1, further comprising a seventh image processor for executing a segmentation process on the extraction image obtained by the sixth image processor.

5. The image processing apparatus according to claim 2, further comprising a seventh image processor for executing a segmentation process on the extraction image obtained by the sixth image processor.

6. The image processing apparatus according to claim 1, wherein an image generated on the basis of a magnetic resonance signal is used as the original image.

7. The image processing apparatus according to claim 6, wherein an image generated on the basis of the magnetic resonance signal obtained by scanning an imaging region including a tumor in a subject and a cerebral ventricle near the tumor by diffusion tensor imaging is used as the original image, in the original image, the first figure corresponds to the tumor, and the second figure corresponds to the cerebral ventricle.

8. An image processing method of performing an imaging process on an original image having a connection figure including a first figure and a second figure connected to the first figure to generate an extraction image of the first figure extracted, said image processing method performed by at least one processor and comprising:
a first image processing step of obtaining a first image in which the connection figure in the original image is selectively extracted by performing a segmentation process on the original image;
a second image processing step of obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained in the first image processing step;
a third image processing step of obtaining a third image by performing a segmentation process so as to selectively extract the third figure in the second image obtained in the second image processing step;
a fourth image processing step of obtaining a fourth image by performing a process of obtaining the difference between the first image obtained in the first image processing step and the third image obtained in the third image processing step;
a fifth image processing step of obtaining a fifth image by determining whether the size of a figure included in the fourth image obtained in the fourth image processing step is equal to or larger than a reference value, and when the size is equal to or larger than the reference value, eliminating the figure from the fourth image and, when the size is less than the reference value, processing the fourth image so as to leave the figure in the fourth image; and
a sixth image processing step of obtaining the extraction image by adding the third image obtained in the third image processing step and the fifth image obtained in the fifth image processing step.

9. The image processing method according to claim 8, further comprising a region-of-interest setting step of setting a region of interest so as to correspond to the first figure in the original image,
wherein in the third image processing step, the third figure in the second image is selectively extracted so as to correspond to the first figure on the basis of positional information of the region of interest set in the original image in the region-of-interest setting step.

10. The image processing method according to claim 9, wherein in the region-of-interest setting step, the region of interest is set on the basis of an instruction from an operator.

11. The image processing method according to claim 8, further comprising a seventh image processing step of executing a segmentation process on the extraction image obtained in the sixth image processing step.

12. The image processing method according to claim 9, further comprising a seventh image processing step of executing a segmentation process on the extraction image obtained in the sixth image processing step.

13. The image processing method according to claim 10, further comprising a seventh image processing step of executing a segmentation process on the extraction image obtained in the sixth image processing step.

14. The image processing method according to claim 8, wherein an image generated on the basis of a magnetic resonance signal is used as the original image.

15. The image processing method according to claim 14, wherein an image generated on the basis of the magnetic resonance signal obtained by scanning an imaging region including a tumor in a subject and a cerebral ventricle near the tumor by diffusion tensor imaging is used as the original image, in the original image, the first figure corresponds to the tumor, and the second figure corresponds to the cerebral ventricle.

16. A magnetic resonance imaging apparatus for generating an original image having a connection figure including a first figure and a second figure connected to the first figure on the basis of a magnetic resonance signal obtained by scanning an imaging region in a subject, and executing imaging process on the original image, thereby generating an extraction image of the first figure extracted, said magnetic resonance imaging apparatus comprising:

a first image processor for obtaining a first image in which the connection figure in the original image is selectively extracted by performing a segmentation process on the original image;

a second image processor for obtaining a second image including a third figure separated from the second figure and a fourth figure separated from the first figure in the connection figure by sequentially performing an erosion process and a dilation process in a morphologic operation so as to separate the first and second figures from each other, in the connection figure included in the first image obtained by the first image processor;

a third image processor for obtaining a third image by performing a segmentation process so as to selectively extract the third figure in the second image obtained by the second image processor;

a fourth image processor for obtaining a fourth image by performing a process of obtaining the difference between the first image obtained by the first image processor and the third image obtained by the third image processor;

a fifth image processor for obtaining a fifth image by determining whether the size of a figure included in the fourth image obtained by the fourth image processor is equal to or larger than a reference value, and when the size is equal to or larger than the reference value, eliminating the figure from the fourth image and, when the size is less than the reference value, processing the fourth image so as to leave the figure in the fourth image; and a sixth image processor for obtaining the extraction image by adding the third image obtained by the third image processor and the fifth image obtained by the fifth image processor.

17. The magnetic resonance imaging apparatus according to claim 16, further comprising a region-of-interest setting unit for setting a region of interest so as to correspond to the first figure in the original image, wherein the third image processor selectively extracts the third figure in the second image so as to correspond to the first figure on the basis of positional information of the region of interest set in the original image by the region-of-interest setting unit.

18. The magnetic resonance imaging apparatus according to claim 17, wherein the region-of-interest setting unit sets the region of interest on the basis of an instruction from an operator.

19. The magnetic resonance imaging apparatus according to claim 16, further comprising a seventh image processor for executing a segmentation process on the extraction image obtained by the sixth image processor.

20. The magnetic resonance imaging apparatus according to claim 16, wherein the original image is generated on the basis of the magnetic resonance signal obtained by scanning an imaging region including a tumor in a subject and a cerebral ventricle near the tumor by diffusion tensor imaging, in the original image, the first figure corresponds to the tumor, and the second figure corresponds to the cerebral ventricle.

* * * * *